US005346929A

United States Patent [19]

Guttag

[11] Patent Number: 5,346,929

[45] Date of Patent: Sep. 13, 1994

[54] BIODEGRADABLE PLASTIC AND ARTICLES MADE THEREFROM

[76] Inventor: Alvin Guttag, 6612 Whittier Blvd., Bethesda, Md. 20817

[21] Appl. No.: 853,428

[22] Filed: Mar. 18, 1992

Related U.S. Application Data

[62] Division of Ser. No. 486,217, Feb. 28, 1990, Pat. No. 5,120,089.

[51] Int. Cl.[5] .......................... C08L 3/00; C08L 1/00; C12N 1/26; D21C 1/00; C08K 5/00; C08K 5/56

[52] U.S. Cl. .................................... 523/124; 523/125; 523/128; 523/126; 524/52; 435/248; 435/262; 435/277; 435/254.1; 435/254

[58] Field of Search ............... 435/248, 262, 277, 254; 523/124, 125, 126, 128; 524/52

[56] References Cited

U.S. PATENT DOCUMENTS

| | | | |
|---|---|---|---|
| 3,860,490 | 1/1975 | Guttag | 435/235.1 |
| 4,931,488 | 6/1990 | Chiquet | 523/126 |

*Primary Examiner*—Paul R. Michl
*Assistant Examiner*—LaVonda DeWitt
*Attorney, Agent, or Firm*—Cushman, Darby & Cushman

[57] ABSTRACT

The present invention relates to a biodegradable plastic made from a combination of at least one synthetic plastic polymer, at least one natural polymer and a natural polymer attacking agent and articles made therefrom.

25 Claims, No Drawings

BIODEGRADABLE PLASTIC AND ARTICLES MADE THEREFROM

This is a division of application Ser. No. 07/486,217, filed Feb. 28, 1990, now U.S. Pat. No. 5,120,089.

BACKGROUND OF THE INVENTION

1. Field of the Invention

The present invention relates to a biodegradable plastic and to articles made therefrom. The invention further relates to a method of producing a biodegradable plastic.

2. Background Information

The worldwide popularity of and use of plastic is in large part due to the indestructible nature of plastic. This same characteristic that makes plastic so attractive has lead to serious environmental problems which must now be addressed. The indestructible nature of plastic has lead to disposal problems. In a landfill, a standard polyethylene bag could take 300 to 400 years to be broken down. Landfills are overflowing as accumulating plastics are not degraded. As the garbage piles up in landfills and plastic debris litters the world's oceans, beaches and highways environmental concerns are growing. Innovative ways of reducing the accumulating plastic waste are required.

Plastic comprising polyethylene polymers consist of long chains of carbon atoms, each flanked by two hydrogen atoms. These polymers are tightly intertwined, creating a surface impenetrable to the decay bacteria that are normally responsible for breaking matter down to water, carbon dioxide and humus, or soil compost.

In response to waste disposal problems there has been a demand for biodegradable plastics. In an attempt to meet this demand, blended plastics have been created where synthetic polymers are mixed with naturally occurring polymers such as starch, cellulose or wood. Synthetic blends such as these allow bacteria to colonize on the natural polymers and once established, attack the previously inaccessible plastic polymers. Products using blends of starch and synthetic plastics are commercially available. Garbage bags comprising plastic polymers coated with cornstarch are sold by Archer Daniels Midland Co. in Decatur, Ill. and St. Lawrence Starch Co. in Canada.

Another approach to the creation of biodegradable plastics involves the use of bacterially synthesized plastics. These bacterial plastics are more palatable to other microorganisms than synthetic plastics. The bacteria *Alcaligenes eutrophus* produces large amounts of a plastic polymer called poly-beta-hydroxybutyrate, or PHB. Huge quantities of *A. eutrophus* or genetically engineered bacteria, are cultivated and the PHB harvested. Several companies are pursuing the use of bacterially made plastics such as PHB.

The present invention is considered to provide a significant advance in biodegradable plastics.

SUMMARY OF THE INVENTION

It is accordingly a general object of the present invention to provide a biodegradable plastic.

It is a specific object of the present invention to provide a biodegradable plastic comprising a synthetic plastic polymer, a natural polymer and a polymer attacking agent.

It is another object of the present invention to provide easily degradable articles produced from the biodegradable plastic of this invention.

It is a further object of the present invention to provide a method of producing a biodegradable plastic.

Other objects and advantages of the present invention will be apparent from the description that follows. (All publications mentioned hereunder are incorporated in their entirety herein by reference.)

In one embodiment, the present invention relates to a biodegradable plastic comprising at least one synthetic plastic polymer, at least one natural polymer and a polymer attacking agent.

In another embodiment, the present invention relates to an article formed from a biodegradable plastic comprising at least one synthetic plastic polymer, at least one natural polymer and a polymer attacking agent.

In another embodiment the invention relates to an all synthetic plastic polymer.

DETAILED DESCRIPTION OF THE INVENTION

The present invention relates to a biodegradable plastic comprising at least one synthetic plastic polymer. There also can be present at least one natural polymer and a polymer attacking agent. The present invention further relates to easily degradable articles produced from the biodegradable plastic of this invention. The present invention also relates to a method of producing a biodegradable plastic.

The term "natural polymer" as used herein refers to polymers found in nature which are easily broken down by natural decay bacteria. It includes but is not limited to, particles of starch, inulin, cellulose and wood. These polymers are usually high molecular weight polymers.

The phrase "polymer attacking agent" as used herein includes microorganisms such as bacteria and fungi, which attack and cause the decay of synthetic polymer and/or the natural polymer component of the biodegradable plastic. The use of anaerobic as well as aerobic bacteria is contemplated (e.g., *Aspergillus oryzae*, microorganisms recited in U.S. Pat. Nos. 3,860,490 and 3,767,790, and appropriate microorganisms listed in the American Type Culture Collection Catalogue of Fungi and Yeast 17th Ed. 1987, The Update of the Catalogue of Yeast and Fungi December 1988, The Catalogue of Bacteria and Phages 17th Ed. 1989, and the Catalohas of Microbes and Cells at Work 1st Ed. 1988). The phrase also includes enzymes (e.g., bacterial or fungal) that catalyze such decay (e.g., diastase, amylass and cellulase).

As indicated above, one embodiment of the present invention relates to a biodegradable plastic comprising a synthetic plastic polymer, a natural polymer and a polymer attackin g. agent. The polymer attacking agent can be present e.g. at about 1% by weight of the natural polymer. For example, to a synthetic plastic-starch blend with 0.1 g to 10 g of starch, *Aspergillus oryzae* at a concentration 1% of the starch by weight can be added.

Premature decomposition of the biodegradable plastic can be prevented by incorporating the polymer attacking agent in a water soluble polymer such as, polyvinyl alcohol, polyvinyl-pyrrolidone and ethylene-vinyl alcohol copolymers, from which the natural polymer attacking agent can be leached when the plastic comes into contact with moisture, such as from soil, a disposal area or waterway. The water soluble polymer can be about 1% of the total polymer. When the polymer attacking agent is leached from its polymer, it begins to attack the natural polymer leading to degradation of the article.

In a specific embodiment of the present invention, conventional polymer disintegrating agents can be added to the plastic to speed up the biodegradative process. Such disintegrating agents include those in Hudgin U.S. Pat. No. 4,495,311. The activity of the disintegrating agents can be catalyzed by oxygen liberating agents such as ammonium persulfate or potassium persulfate which can also be incorporated in the biodegradable plastic. These oxygen liberating agents can be protected in hydrophilic polymers to prevent premature release.

In another specific embodiment of the present invention, the biodegradable plastic is acted on by a UV-activated polymer attacking agent such as those in Hudgin U.S. Pat. No. 4,495,311. Articles made of such plastic should be exposed to sunlight or an UV radiation source for a sufficient time to activate degradation before being buried at a waste disposal site.

In a further specific embodiment of the present invention, the biodegradable plastic also can include an agent that attacks the natural polymer only when wet. Such agents include acidic salts such as ammonium chloride, ammonium sulfate, glycine hydrochloride, $\alpha$-alanine hydrochloride and $\beta$-alanine hydrochloride. Such agents can be encapsulated in hydrophilic polymers to prevent premature activation.

In yet a further specific embodiment, a microbial polymer attacking agent can be present in or encapsulated in dry culture media.

In another specific embodiment of the present invention, spore forming microorganisms are used in formulating the biodegradable plastic. This is particularly useful in cases where, during the plastic forming process, the plastic is subjected to elevated temperatures for prolonged periods. Articles made by processes requiring heat exposure include films, sheets, cups, containers and toys.

The biodegradable plastic of this invention can be used for the formation of articles, including but not limited to, bottles, toys, gloves, boxes, dishes, bowls, syringes, cups and diapers.

Diapers made by conventional methods, for example, U.S. Pat. Nos. 3,848,594; 3,860,003; 4,081,301; 4,573,986; 4,578,071; 4,610,678; 4,573,203; 4,654,039; 4,662,875; 4,673,402; 4,710,189; and 4,515,495 can have in addition in their plastic layer a hydrocarbon-degrading agent and in their absorbent cotton layer a cellulose-degrading agent such as cellulase or a harmless microorganism that forms cellulase.

When the biodegradable plastic is molded into an article, such as containers for use in containing consumable products such as milk and yogurt, an additional internal layer which contacts the food or the like will be present. Such an internal layer will not include a polymer attacking agent. When such an article is destroyed, for example, by being cut up, the polymer attacking agent will be in contact with the inner layer and decay of the entire container will proceed.

While the foregoing invention has been described in some detail for purposes of clarity and understanding, it will be clear to one skilled in the art from a reading of this disclosure that various changes in form and detail can be made without departing from the true scope of the invention. For example, one skilled in the art will appreciate that the addition of concentrated oxygen or acid to the biodegradable plastic under appropriate conditions can facilitate breakdown of the plastic. One skilled in the art will also appreciate that biodegradable paper cups and other containers can be produced in which a natural polymer, such as cellulose, and a polymer attacking agent, such as cellulase, are incorporated into the cup during the production of the paper or during the formation of the cup. If a hydrocarbon coating such as wax is desired, a degrading organism active on the coating material can be incorporated therein.

Illustrative polymers which can be treated according to the invention include polyethylene, polystyrene, polypropylene, ethylene-propylene copolymer, natural rubber, synthetic rubber, e.g., butadiene-styrene copolymer, polyisoprene, polybutadine, polyamylene as well as cellulose.

It has been observed that cellulose containing waste, e.g. newspapers, will remain for long periods of time in waste disposal areas even though cellulose attacking organisms or enzymes are present. The reason for this is that water needs to be present for the organism (whether they be anaerobic or aerobic) to grow or to activate the enzyme. Water does not normally penetrate deep into these waste areas. To enable the disintegration of the cellulose waste water must be applied into the interior of the waste, preferably all the way to the bottom. This can be accomplished by spraying water on the waste simultaneously with or alternately with turning over or churning the waste to expose dry or substantially dry areas to the water. Then the microorganism and/or enzyme can act.

What is claimed is:

1. A biodegradable plastic comprising at least one synthetic plastic polymer, at least one natural polymer and a polymer attacking agent for said synthetic plastic polymer or said natural polymer wherein said polymer attacking agent comprises a microorganism or an enzyme.

2. The biodegradable plastic according to claim 1 wherein said polymer attacking agent comprises a microorganism.

3. The biodegradable plastic according to claim 1 wherein said polymer attacking agent is an enzyme.

4. A biodegradable plastic according to claim 1 wherein the polymer attacking agent comprises a microorganism and there is incorporated in the plastic a dry culture medium for a microorganism.

5. The biodegradable plastic according to claim 2 wherein said microorganism is a species of bacteria or fungi.

6. The biodegradable plastic according to claim 1 wherein said polymer attacking agent is present in a water soluble or water swellable polymer.

7. The biodegradable plastic according to claim 2 wherein said microorganism is a spore forming microorganism.

8. The biodegradable plastic according to claim 1 which further comprises a synthetic polymer disintegrating chemical agent.

9. The biodegradable plastic according to claim 1 wherein said natural polymer is starch or cellulose.

10. An article formed from the biodegradable plastic according to claim 1.

11. The biodegradable plastic according to claim 1 wherein the natural polymer comprises starch, inulin or cellulose and the polymer attacking agent is a microorganism or enzyme which will attack said starch, inulin or cellulose.

12. The biodegradable plastic according to claim 11 wherein the biodegradable plastic is an article which is a film, sheet, container, toy, diaper or glove.

13. The biodegradable plastic according to claim 1 wherein the polymer attacking agent comprises an anaerobic microorganism.

14. An article according to claim 10 which is a diaper.

15. A biodegradable plastic container comprising at least one synthetic plastic polymer and a polymer attacking agent for said synthetic plastic polymer comprising a microorganism or an enzyme.

16. A container according to claim 15 having an interior surface of the container coated with an internal layer of a polymer free of said microorganism or enzyme attacking agent whereby the attaching agent free internal layer of the container only becomes exposed to the attacking agent when the container is destroyed so that said interior surface can contact said attacking agent.

17. The biodegradable plastic container according to claim 15 wherein said polymer attacking agent comprises a microorganism.

18. The biodegradable plastic container according to claim 17 including a water-free microorganism growth medium together with the microorganism whereby when the combination of a microorganism and growth medium contacts water the microorganism will grow.

19. A container according to claim 15 which is a cup, bottle, box, dish, bowl or syringe.

20. A container according to claim 16 wherein the container contains food and the coating prevents the food from contacting the polymer attacking agent.

21. A container according to claim 20 which is a milk bottle and the food is milk.

22. A biodegradable plastic container according to claim 15 wherein the polymer attacking agent comprises a microorganism and the plastic has incorporated therein a dry culture medium for the microorganism.

23. The biodegradable plastic container according to claim 15 wherein said polymer attacking agent is present in a water soluble or water swellable polymer.

24. The biodegradable container according to claim 15 wherein the polymer attacking agent is a spore forming microorganism.

25. The biodegradable container according to claim 15 wherein said biodegradable container is free of natural polymer.

* * * * *